(12) United States Patent
Ellis

(10) Patent No.: US 9,295,746 B2
(45) Date of Patent: Mar. 29, 2016

(54) ADD ON FILTER FOR PACKAGE AIR HANDLING UNIT

(71) Applicant: RGF Environmental Group, Inc., Riviera Beach, FL (US)

(72) Inventor: Walter B. Ellis, Jupiter, FL (US)

(73) Assignee: RGF ENVIRONMENTAL GROUP, INC., Riviera Beach, FL (US)

( * ) Notice: Subject to any disclaimer, the term of this patent is extended or adjusted under 35 U.S.C. 154(b) by 49 days.

(21) Appl. No.: 14/098,123

(22) Filed: Dec. 5, 2013

(65) Prior Publication Data

US 2015/0157755 A1    Jun. 11, 2015

(51) Int. Cl.
*B03C 3/01* (2006.01)
*B01D 47/00* (2006.01)
*A61L 9/00* (2006.01)
*A61L 2/10* (2006.01)
*B01D 41/00* (2006.01)
*A61L 9/20* (2006.01)

(52) U.S. Cl.
CPC ... *A61L 9/00* (2013.01); *A61L 2/10* (2013.01); *A61L 9/205* (2013.01); *B01D 41/00* (2013.01); *A61L 2209/14* (2013.01); *A61L 2209/16* (2013.01); *Y10T 29/49826* (2015.01)

(58) Field of Classification Search
CPC ............ B01D 46/00; B03C 3/00; A61L 9/00; A61L 9/20; A61L 9/205
USPC ........... 422/24, 186; 96/58, 224, 361; 95/214, 95/273
See application file for complete search history.

(56) References Cited

U.S. PATENT DOCUMENTS 4,917,862 A * 4/1990 Kraw et al. ...................... 422/4

* cited by examiner

*Primary Examiner* — Monzer R Chorbaji
(74) *Attorney, Agent, or Firm* — Rothwell, Figg, Ernst & Manbeck, P.C.

(57) ABSTRACT

The present invention relates to an add on filter for a packaged air handling unit, such as a heating, ventilation and/or air conditioning unit, and method incorporating an add on filter for applying ultraviolet light to an environment to create oxidizing agents for killing microbes, such as bacteria, mold, and viruses, and for destroying odors. The add on filter may be coupled to the blower housing of existing packaged heating, ventilation and/or air conditioning units. The add on filter includes an ultraviolet light source for emitting a broad spectrum of ultraviolet light and a catalytic target structure mechanically coupled to the ultraviolet light source. The system and method result in the production of Hydroxyl Radicals, Super Oxide ions and Hydro Peroxide for killing microbes.

14 Claims, 13 Drawing Sheets

ADD ON FILTER FOR PACKAGE AIR HANDLING UNIT

TECHNICAL FIELD

The present invention relates generally to the field of air filtration and, more particularly, to an add on filter for an air handling unit and a method for applying the same. The add on filter is mounted to a blower in an air handling unit and applies ultraviolet light to an environment to create oxidizing agents for killing microbes, such as bacteria, mold, and viruses, and for destroying odors.

BACKGROUND

Traditional air filtration systems are not effective for treating many types of microbials (e.g., bacteria, germs, viruses, fungi, spores and mold) and gases (e.g., benzene, formaldehyde, chloroform, hydrogen sulfide, ammonia). Hydroperoxides are very effective at destroying harmful microbials in the air and on surfaces through a process called cell lysing or by changing its molecular structure. Hydroperoxides are also effective at rendering gases harmless by changing their molecular structure. The present invention treats microbials and gases in package air handling units, such as a heating, ventilation and/or air conditioning unit.

SUMMARY

Particular embodiments of the present invention are directed to an add on filter and method incorporating such an add on filter for applying ultraviolet light to an air handling unit for killing microbes, such as bacteria, mold, and viruses, and for destroying odors.

According to particular embodiments of the present invention, an add on filter for a packaged heating, ventilation and/or air conditioning unit including a blower and a blower housing comprising a filter housing is provided. The add on filter also includes a first mounting unit coupled to the filter housing and a first magnet to couple the first mounting unit to the blower housing. The add on filter further includes a second mounting unit coupled to the filter housing and a second magnet to couple the second mounting unit to the blower housing. The distance between the first magnet and the second magnet is adjustable. The add on filter also includes a device disposed in the filter housing for the formation of advanced oxidation product. The device for formation of advanced oxidation product includes an ultraviolet light source for emitting a broad spectrum of ultraviolet light and a first catalytic target structure mechanically coupled to the ultraviolet light source.

In some embodiments, the first mounting unit is approximately V-shaped and the second mounting unit is approximately V-shaped. Each of the first mounting unit and the second mounting unit includes at least two magnets. Each magnet of each mounting unit is independently adjustable relative to the respective mounting unit. In some embodiments, the first mounting unit is shaped to be mounted on a plurality of blower housings, wherein each of the plurality of blower housings includes a different curvature of radius.

In some embodiments, the first mounting unit includes a first rail and a portion of the first magnet is positioned in the first rail. The second mounting unit includes a second rail and a portion of the second magnet is positioned in the second rail. The first magnet is slidable relative to the first rail, and the second magnet is slidable relative to the second rail. In some embodiments, the first mounting unit includes a third rail and a portion of a third magnet is positioned in the third rail, and the second mounting unit includes a fourth rail and a portion of a fourth magnet is positioned in the fourth rail. The third magnet is slidable relative to the third rail, and the fourth magnet is slidable relative to the fourth rail. When the add on filter is mounted to the blower housing, the first magnet is fixed relative to the first rail, the second magnet is fixed relative to the second rail, the third magnet is fixed relative to the third rail and the fourth magnet is fixed relative to the fourth rail.

In some embodiments, the filter housing includes a first protrusion and a second protrusion. The first protrusion forms a first rail with the first mounting unit and a portion of the first magnet is positioned in the first rail. The second protrusion forms a second rail with the second mounting unit and a portion of the second magnet is positioned in the second rail.

In some embodiments, the filter housing includes a plurality of openings in a portion of the filter housing surrounding the device for formation of advanced oxidation product. The portion of the filter housing including a plurality of openings forms a second catalytic target structure.

According to particular embodiments of the present invention, a system for filtering air in a packaged heating, ventilation and/or air conditioning unit comprising a blower and a blower housing includes an add on filter coupled to the blower housing to produce an oxidation agent. The add on filter comprises a filter housing. The add on filter also includes a first mounting unit coupled to the filter housing and a first magnet to couple the first mounting unit to the blower housing. The add on filter further includes a second mounting unit coupled to the filter housing and a second magnet to couple the second mounting unit to the blower housing. The distance between the first magnet and the second magnet is adjustable. The add on filter also includes a device disposed in the filter housing for the formation of advanced oxidation product. The device for formation of advanced oxidation product includes an ultraviolet light source for emitting a broad spectrum of ultraviolet light and a first catalytic target structure mechanically coupled to the ultraviolet light source.

In another aspect, certain embodiments of the present invention are directed to a method for filtering air in a packaged heating, ventilation and/or air conditioning unit including a blower with a blower housing. The method includes a step of providing an add on filter including a first mounting unit with a first magnet and a second mounting unit with a second magnet. The method also includes a step of adjusting a distance between the first magnet and the second magnet such that the distance between the first and second magnets is not greater than a length of the blower housing. The method further includes a step of mounting the add on filter to the blower housing via the first magnet and the second magnet.

BRIEF DESCRIPTION OF THE DRAWINGS

The accompanying drawings, which are incorporated herein and form part of the specification, illustrate various embodiments of the present disclosure and, together with the description, further serve to explain the principles of the disclosure and to enable a person skilled in the pertinent art to make and use the embodiments disclosed herein. In the drawings, like reference numbers indicate identical or functionally similar elements.

DETAILED DESCRIPTION

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art. Further, the terms and phrases used herein are not intended to be limiting; but rather, to provide an understandable description of the invention.

According to particular embodiments of the present invention, an add on filter for a packaged air handling unit, such as a heating, ventilation and/or air conditioning unit, includes a device for formation of an advanced oxidation product, such as a PHI cell. The add on filter may be coupled to the blower housing of a packaged air handling unit. The device for formation of an advanced oxidation product includes an ultraviolet light source for emitting a broad spectrum of ultraviolet light and a catalytic target structure mechanically coupled to the ultraviolet light source. The target catalytic structure comprises a multi-metallic catalytic and hydrophilic material, and the hydrophilic surface attracts and absorbs moisture from the surrounding air. The broad spectrum ultraviolet light includes multiple bands of ultraviolet light at about 185 nm, 254 nm, 320 nm, 365 nm, 380 nm, 400 nm and 480 nm wavelength. The ultraviolet energy at 254 nm and above strikes the target structure and activates production of Hydroxyl Radicals, Super Oxide ions and Hydro Peroxide on the surface. The ultraviolet energy at 185 nm is sufficient to split oxygen molecules to form ozone gas. These ozone molecules in the air are then reduced back to oxygen via decomposition process initiated by the 254 nm ultraviolet light energy, which results in the production of Hydroxyl Radicals, Super Oxide ions and Hydro Peroxide similar to the surface reaction. This process is described in further detail in co-owned U.S. Pat. No. 7,988,932, the entire disclosure of which is herein incorporated by reference.

Figure 1:
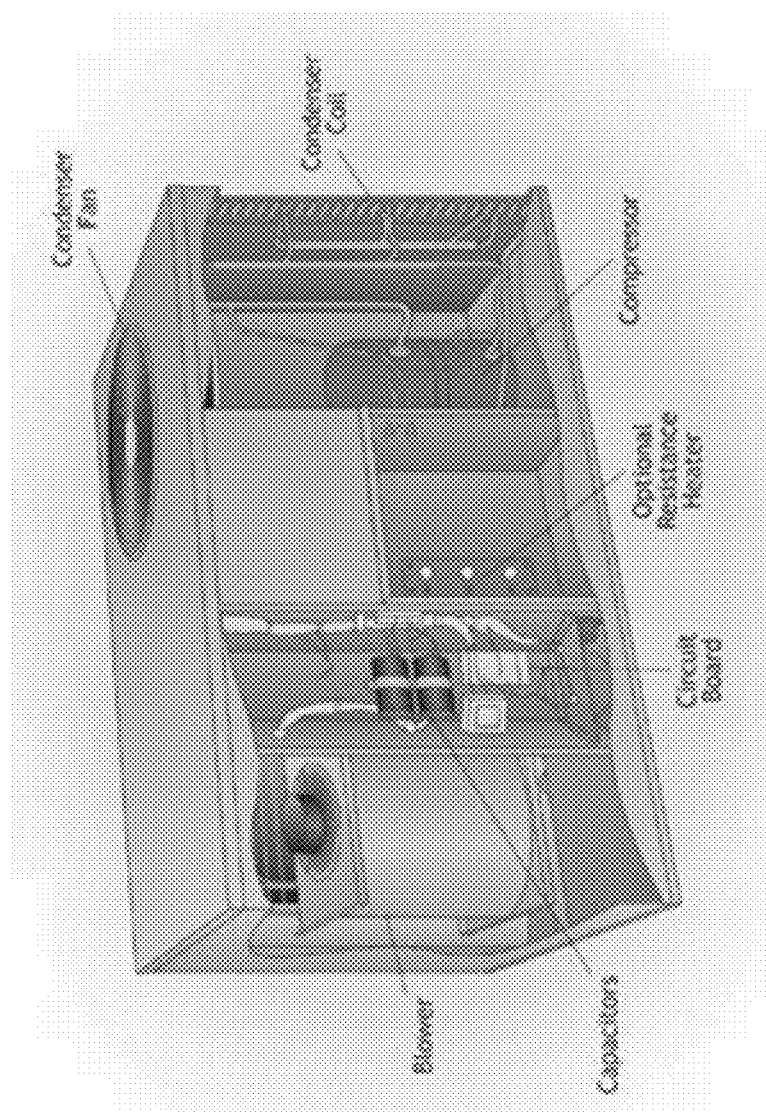
FIG. 1 Illustrates a perspective view of a packaged air handling unit, such as a heating, ventilation and/or air conditioning unit, known in the art.

FIG. 1 illustrates a packaged air handling system, such as a heating, ventilation and/or air conditioning unit, known in the art. The air handling system 100 includes a blower 102, which includes a blower housing 104. The blower 102 is configured to move air through the air handling unit 100. The blower housing 104 surrounds the blower 102 and is composed of a metallic material. The air handling system 100 also includes a condenser fan 106, condenser coils 108, a compressor 110, a resistance heater 112 and a circuit board 114.

Figure 2:
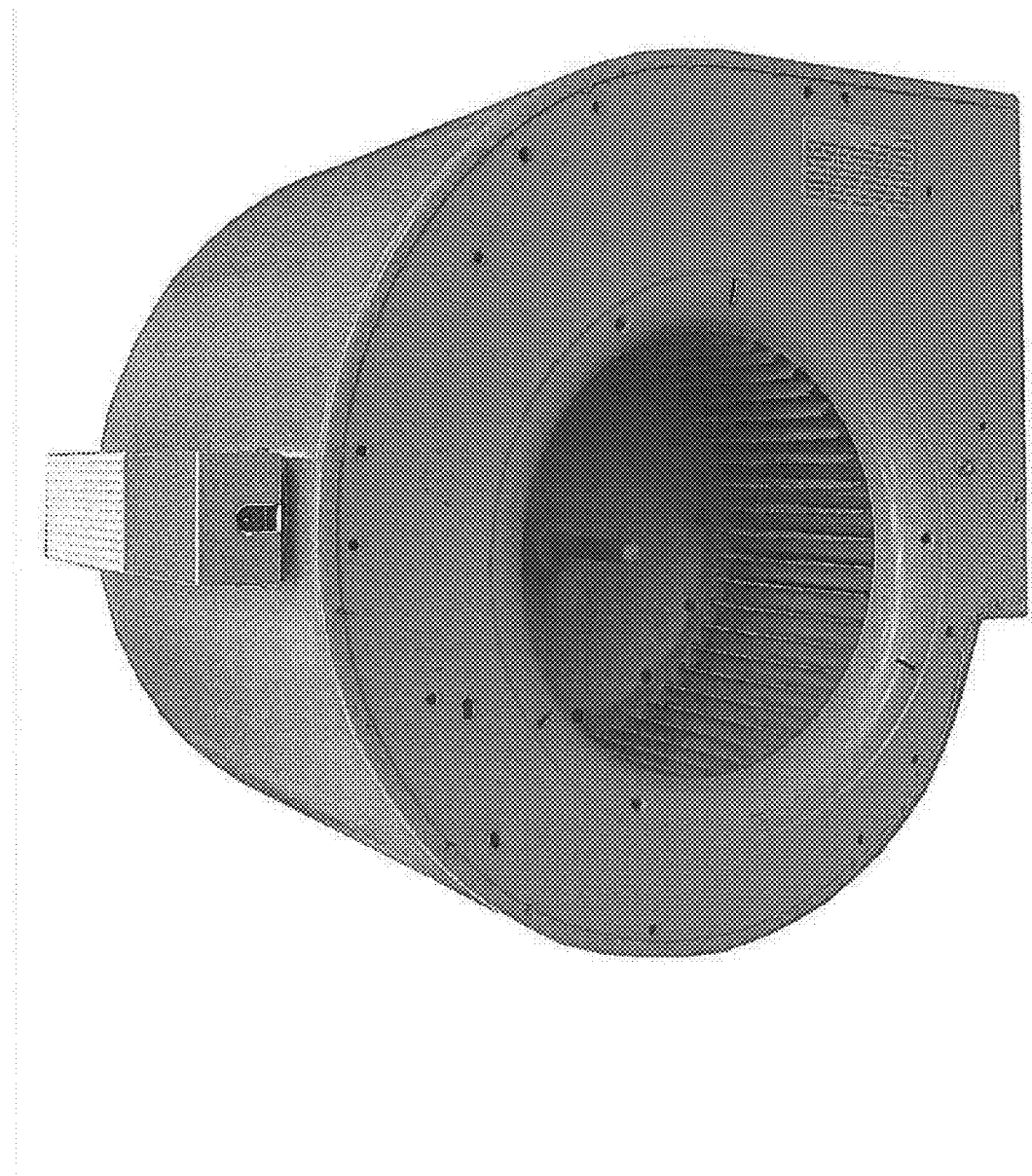
FIG. 2 illustrates a perspective view of an add on filter mounted on a blower housing in accordance with exemplary embodiments of the present invention.
Figure 3:
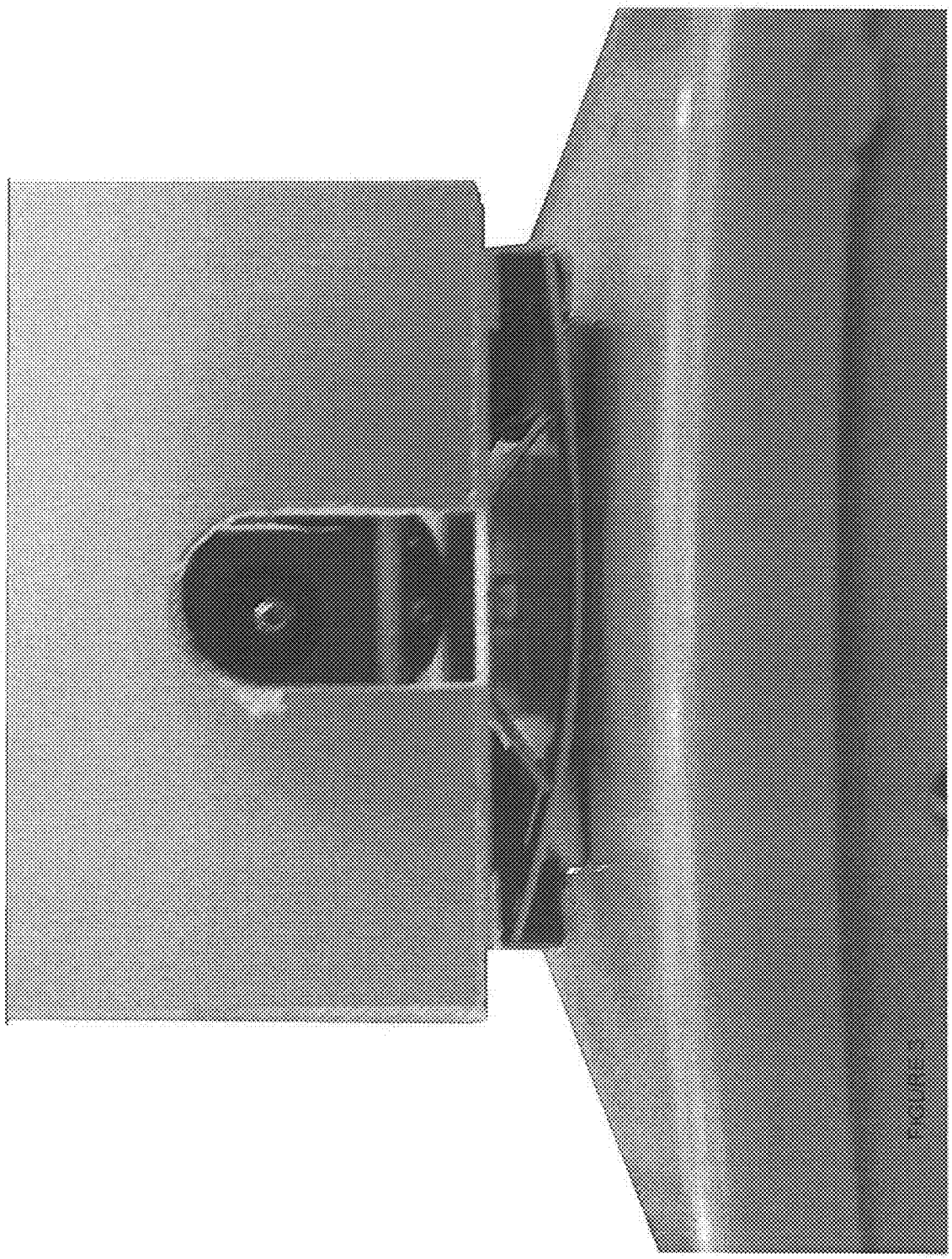
FIG. 3 illustrates a side view of an add on filter mounted on a blower housing in accordance with exemplary embodiments of the present invention.

FIGS. 2 and 3 illustrate an add on filter 200 mounted on a blower housing 104 of an air handling unit according to particular embodiments of the present invention. The add on filter 200 includes a filter housing 202 surrounding a device for formation of an advanced oxidation product or PHI cell 204 which treats microbials and gases. The housing 202 is configured to allow air to move through the add on filter 202 and be treated by the PHI cell 204. The add on filter 200 is mounted on the blower housing 104 by magnets on a first mounting unit 206 and a second mounting unit 208 (see FIG. 4), which will be discussed in further detail below. The add on filter 200 is positioned on the blower housing 104 such that air traveling through the air handling unit 100 is treated with the advanced oxidation product.

Figure 4:
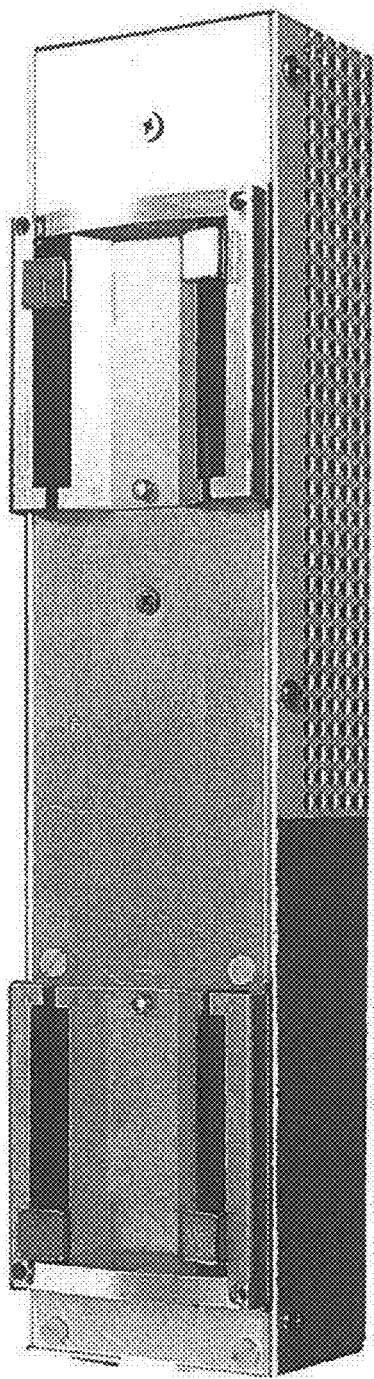
FIG. 4 illustrates a perspective view of an add on filter in accordance with exemplary embodiments of the present invention.
Figure 5:
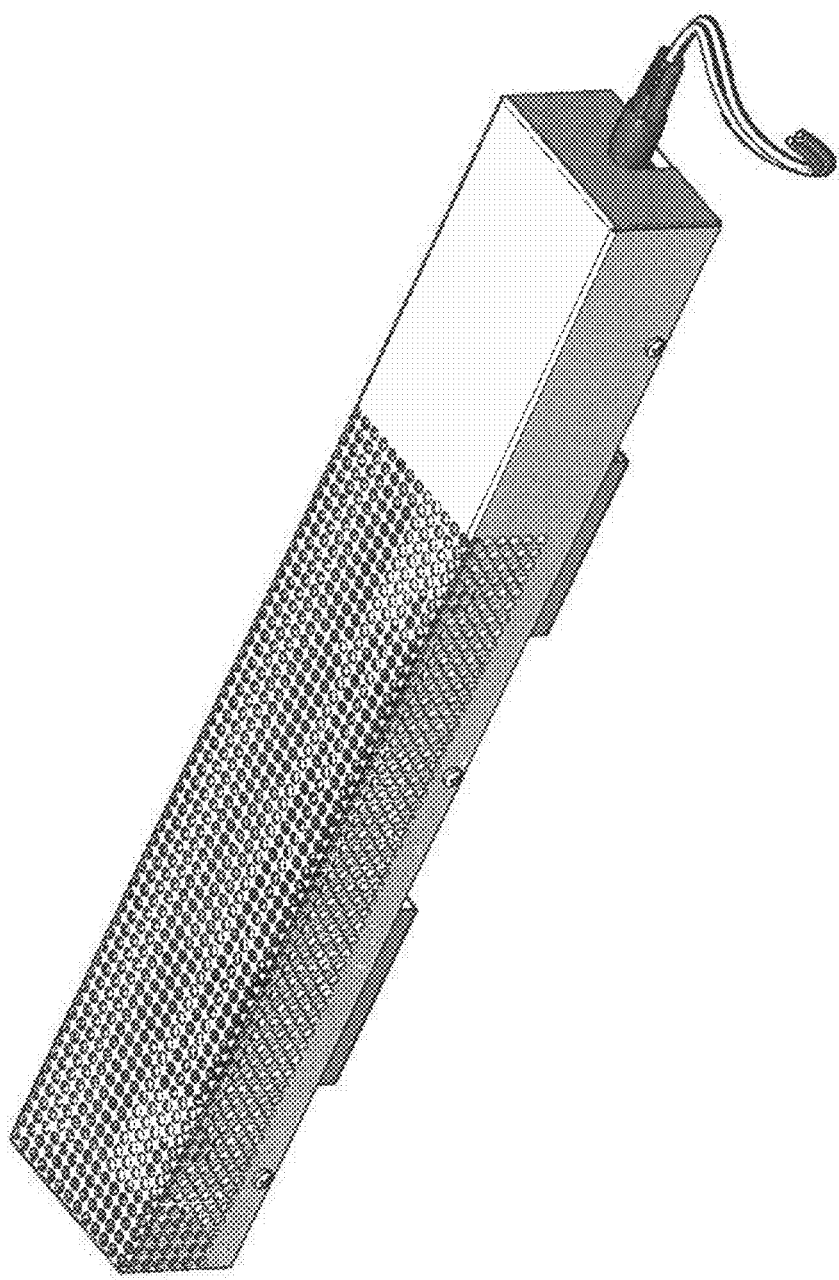
FIG. 5 illustrates a perspective view of an add on filter in accordance with exemplary embodiments of the present invention.
Figure 6:
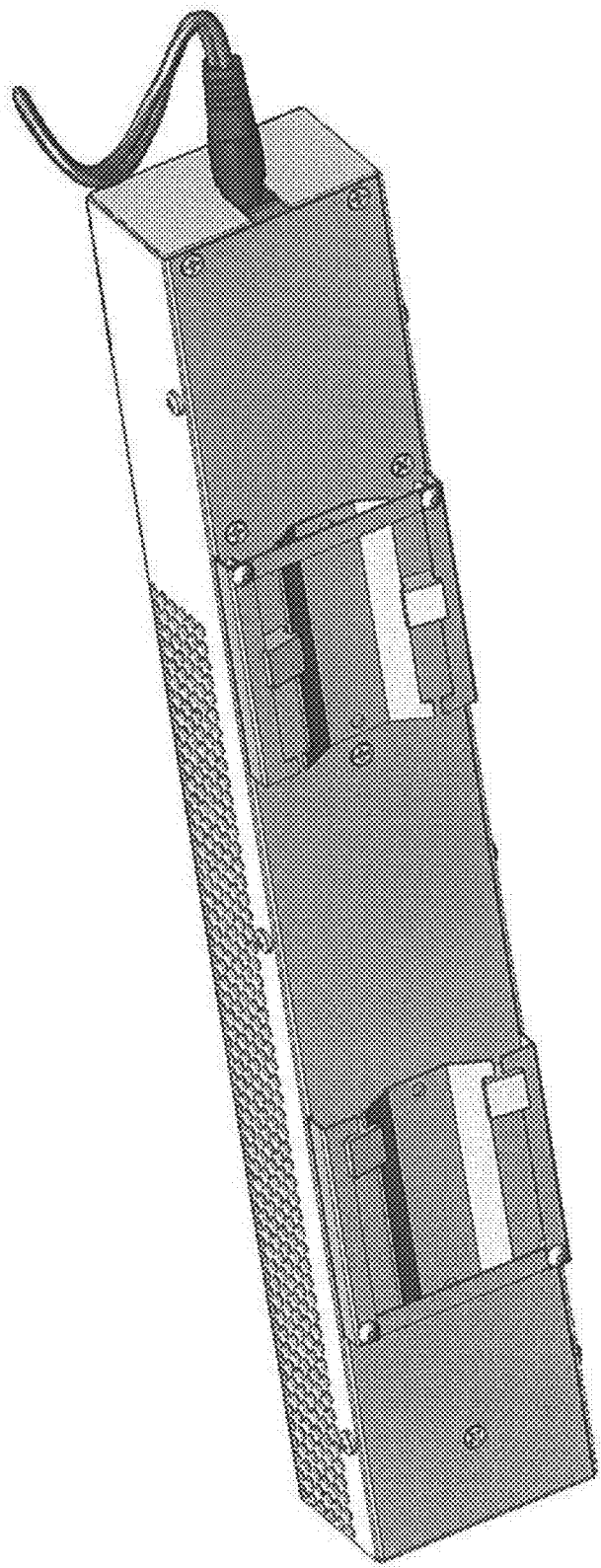
FIG. 6 illustrates a perspective view of an add on filter in accordance with exemplary embodiments of the present invention.
Figure 10:
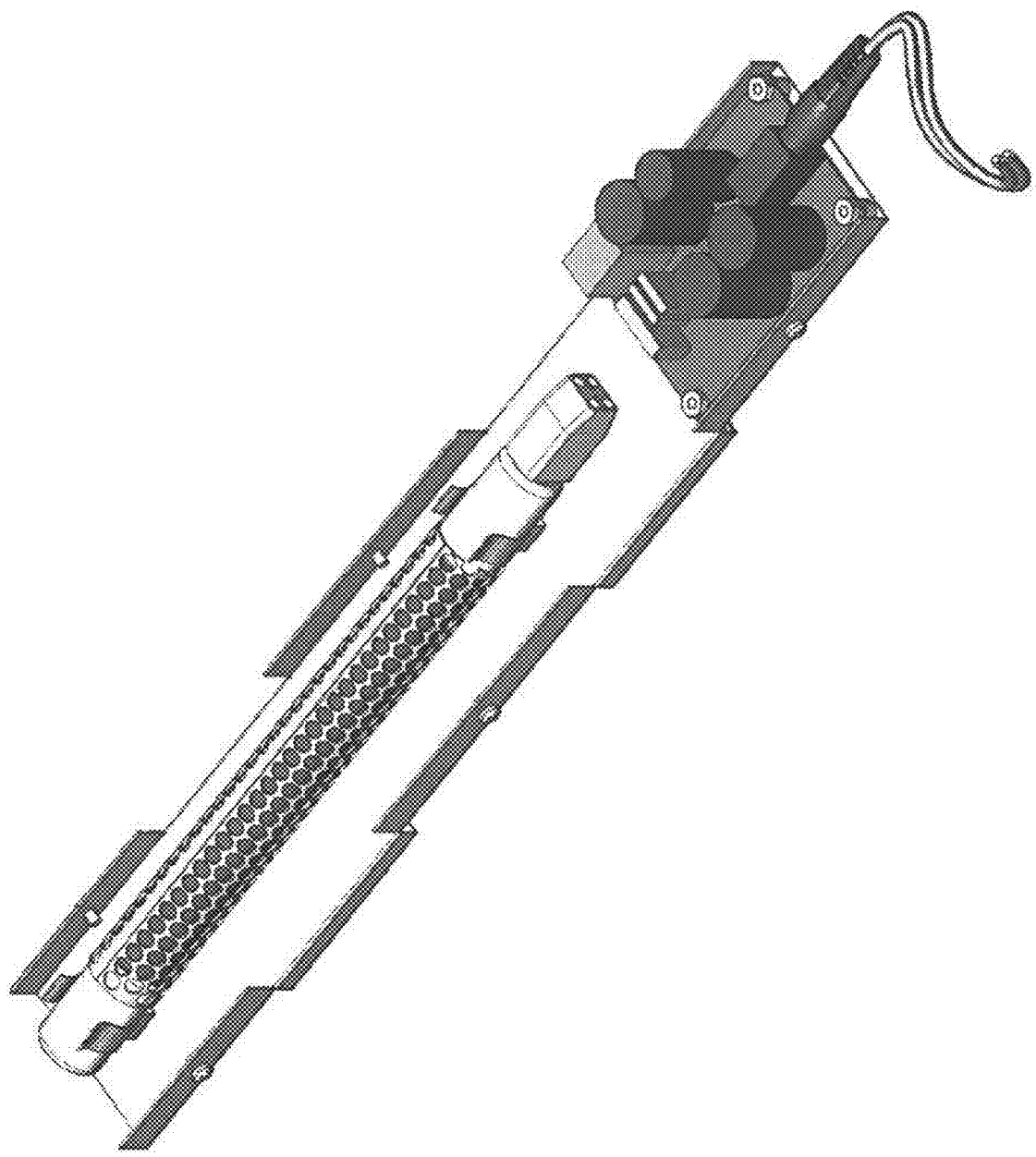
FIG. 10 illustrates a perspective view of a device for formation of advanced oxidation product without the housing and a base of an add on filter in accordance with exemplary embodiments of the present invention.
Figure 11:
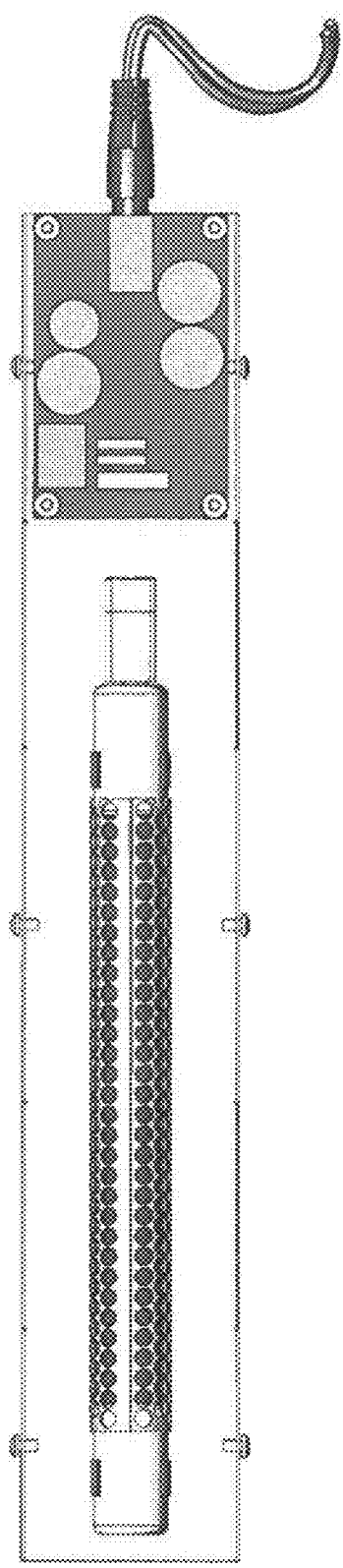
FIG. 11 illustrates a top view of a device for formation of advanced oxidation product without the housing and a base of an add on filter in accordance with exemplary embodiments of the present invention.
Figure 12:
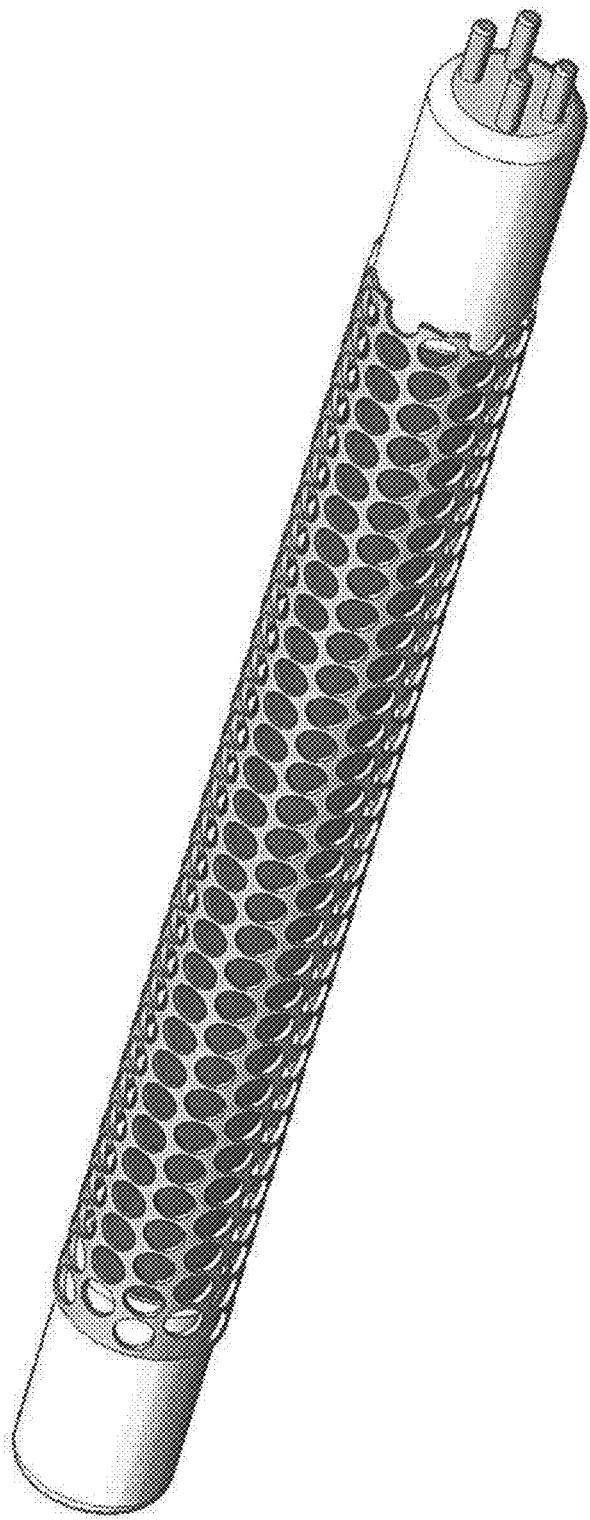
FIG. 12 illustrates a perspective view of a device for formation of advanced oxidation product of an add on filter without the housing in accordance with exemplary embodiments of the present invention.
Figure 13:
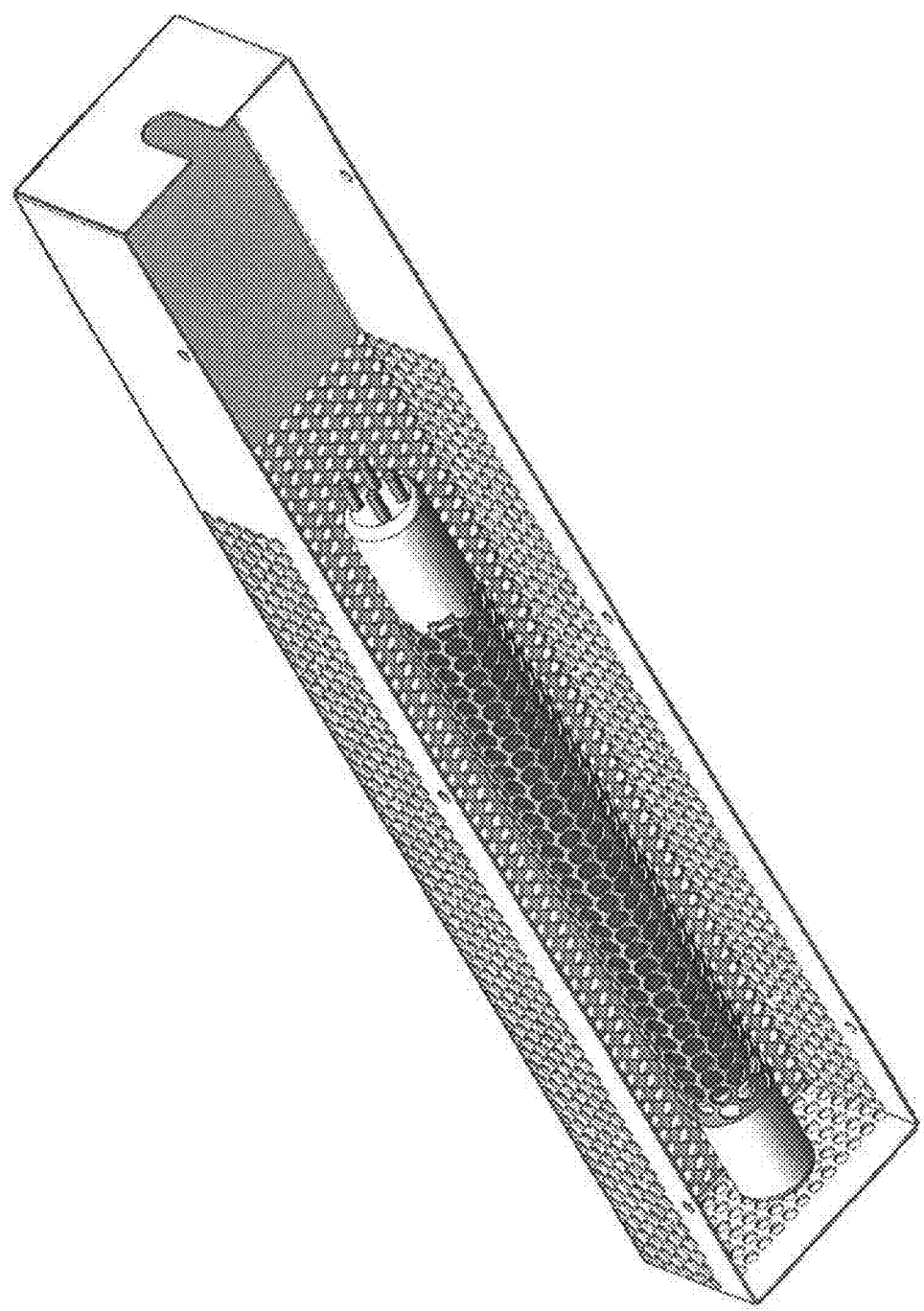
FIG. 13 illustrates a perspective view of a device for formation of advanced oxidation product and a housing of an add on filter in accordance with exemplary embodiments of the present invention.

FIGS. 4-6 illustrate an add on filter 200 according to particular embodiments of the present invention. The add on filter 200 includes a filter housing 202, a PHI cell 204, a first mounting unit 206, a second mounting unit 208, a base 210 and a plurality of openings in the filter housing 212. The PHI cell 204 is positioned within the filter housing 202 such that the plurality of openings 212 surround the cell 204. The plurality of openings 212 allow air to pass through the add on filter 200 and be treated by the PHI cell 204. In an embodiment of the present invention, the PHI cell 204 is mounted to the base 210, as described in further detail below with reference to FIGS. 10 and 11. The first mounting unit 206 includes a first rail 400 and a second rail 402, and the second mounting unit 208 includes a third rail 408 and a fourth rail 410. Each rail is an opening in its respective mounting unit. The first mounting unit 206 also includes a first magnet 404 configured to engage the first rail 400 and a second magnet 406 configured to engage the second rail 402. The second mounting unit 208 includes a third magnet 412 configured to engage the third rail 408 and a fourth magnet 414 configured to engage the fourth rail 410. Each magnet 404, 406, 412 and 414 is approximately I-shaped, and each magnet is positioned in its respective rail 400, 402, 408 and 410 such that the narrow middle portion of the magnet is positioned in the rail. Each magnet 404, 406, 412 and 414 is slidable relative to its respective rail 400, 402, 408 and 410 over the length of the rail.

Each mounting unit 206 and 208 is approximately V-shaped, i.e., the portion between the rails is concave. The shape of each mounting unit 206 and 208 and the position of the rails 400, 402, 408 and 410 in their respective mounting unit allow the add on filter 200 to be mounted on blower housings 104 with different curvatures of radius. In particular, each of the magnets 404, 406, 412 and 414 is strong enough to pull itself, its respective rail and the mounting unit surrounding it towards the surface of the blower housing 104.

The strength of the magnets 404, 406, 412 and 414 allows for the mounting units 206 and 208 to adapt to different curvatures of radius. Also, the strength of the magnets 404, 406, 412 and 414 is such that it creates friction with the portion of the mounting units 206 and 208 surrounding the rails 400, 402, 408 and 410 sufficiently strong to prevent the magnets from sliding relative to the rails, i.e., when the add on filter 200 is mounted to a blower housing 104, the magnets 404, 406, 412 and 414 become locked in place. In contrast, when the add on filter 200 is not mounted to a blower housing 104, each of the magnets 404, 406, 412 and 414 are easily moved relative to its respective rail 400, 402, 408 and 410. Prior to mounting the add on filter 200 on a blower housing 104, the position of each of the magnets 404, 406, 412 and 414 may be adjusted relative to its respective rail 400, 402, 408 and 410 such the distance between the magnets of the first mounting unit 206 and the magnets of the second mounting unit 208 may be adjusted to allow the add on filter 200 to be mounted on blower housings 104 of various lengths.

Figure 7:
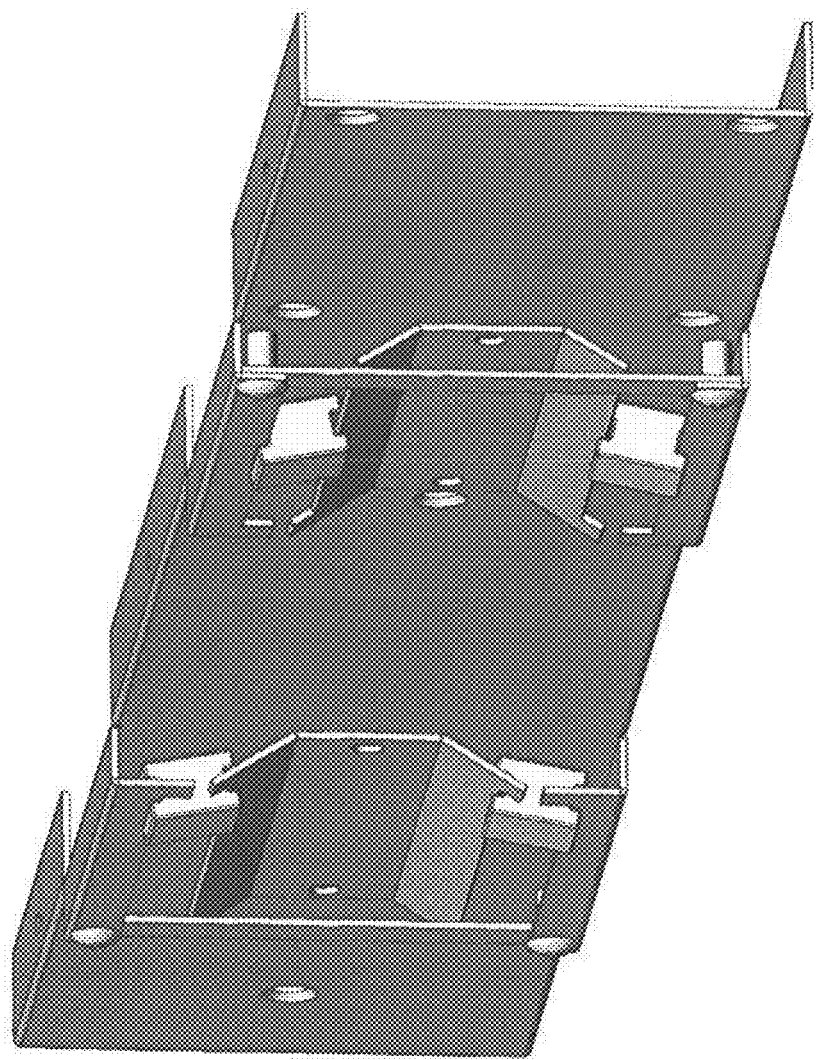
FIG. 7 illustrates a base of an add on filter in accordance with exemplary embodiments of the present invention.
Figure 8:
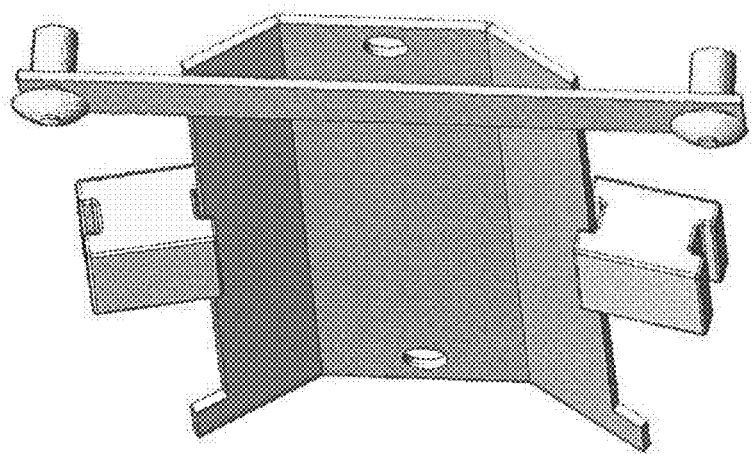
FIG. 8 illustrates a detailed view of a mounting unit of the add on filter in accordance with exemplary embodiments of the present invention.
Figure 9:
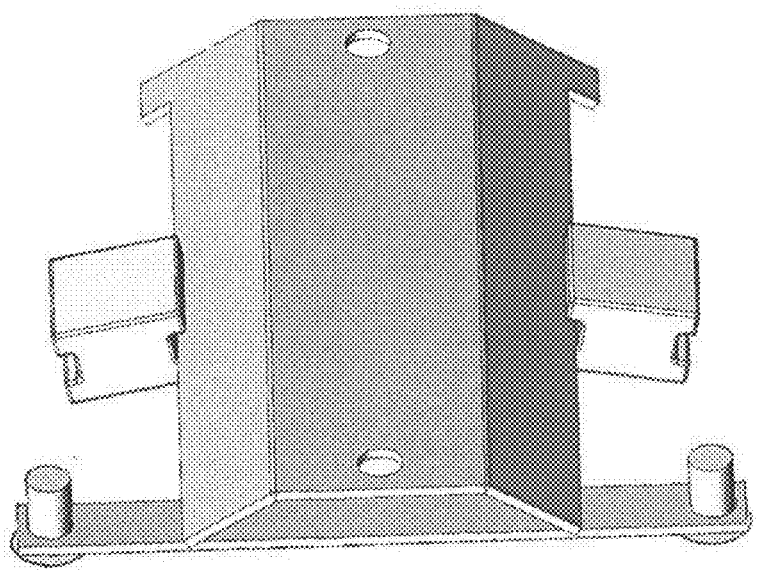
FIG. 9 illustrates a detailed view of a mounting unit of an add on filter in accordance with exemplary embodiments of the present invention.

FIGS. 7-9 illustrate detailed views of mounting units 206 and 208 of an add on filter according to particular embodiments of the present invention. The mounting units 206 and 208 are coupled to the base 210 of the filter housing. Each mounting unit 206 and 208 includes an inner member 700, a transverse member 702 and outer members 712 and 714. It should be understood that while the description below is directed to the first mounting unit 206, the components described are the same in both mounting units 206 and 208. The inner member 700 is positioned in between the outer members 712 and 714 and the transverse member 702 is coupled to the outer members 712 and 714 such that it extends across the inner member 700. In an embodiment of the present invention, the transverse member 702 may be bent towards the inner member when assembled, which allows for fitting the curvature of the blower. The inner member 700 includes a first angled member 704, a center member 706 and a second angled member 708. The first and second angled members 704 and 708 are coupled to opposite sides of the center member 706, and each of the angled members 704 and 708 extend from the center member 706 at an angle away from the base 210. The first angled member 704 forms a rail 400 with the outer member 714. The transverse member 702 forms a first end of the rail 400 and a protrusion extending from the outer member 714 and a protrusion extending from the first angled member 704 form a second end of the rail 400. Similarly, the second angled member 708 forms a rail 402 with the outer member 712, and the ends of the rail 402 are defined by the transverse member 702 and protrusions extending from the second angled member 708 and the outer member 712.

The mounting units 206 and 208 are coupled to base 210. The inner members 710 of the mounting units 206 and 208 may be coupled to the base 210 via coupling members (e.g., screws or bolts) engaged with openings 710 and corresponding openings in the base 210. The transverse members 702 may be coupled to the outer members 712 and 714 via a coupling member (e.g., screws or bolts), and the coupling members may extend into the base 210. The outer members 712 and 714 may be welded to the base 210. In another embodiment of the present invention, the inner member 700, the transverse member 702, and the outer members 712 and 714 may be a single unit coupled to the base 210.

FIGS. 10-13 illustrate a device for formation of an advanced oxidation product 204 without the housing according to particular embodiments of the present invention. The device for formation of an advanced oxidation product or PHI cell 204 includes an ultraviolet light source 1000, a target structure 1002, a connector 1004, a ballast 1006 and a cord 500. The PHI cell 204 is coupled to the base by coupling member 108, such as clips configured to engage the ends of the PHI cell 204. The ultraviolet light source 1000 is a cylindrical bulb. The target structure 1002 surrounds the light source 1000 provides a surface area to be contacted by the ultraviolet light emitted by the source 1000. The ultraviolet light source 1000 emits ultraviolet light at multiple bands: about 185 nm, 254 nm, 320 nm, 365 nm, 380 nm, 400 nm and 480 nm wavelength. The target catalytic structure 1002 comprises a multi-metallic catalytic and hydrophilic material, and the hydrophilic surface attracts and absorbs moisture from the surrounding air. The ultraviolet energy at 254 nm and above strikes the target structure 902 and activates production of Hydroxyl Radicals, Super Oxide ions and Hydro Peroxide on the surface. The ultraviolet energy at 185 nm is sufficient to split oxygen molecules to form ozone gas. These ozone molecules in the air are then reduced back to oxygen via decomposition process initiated by the 254 nm ultraviolet light energy, which results in the production of Hydroxyl Radicals, Super Oxide ions and Hydro Peroxide similar to the surface reaction. The ultraviolet light source 1000 is supplied energy by the ballast 1006 via the cord 500. The ballast 1006 is connected to the ultraviolet light source 1000 via the connector 1004.

In an embodiment of the present invention, the portion of the filter housing 102 surrounding the PHI cell 204 and including a plurality of openings 212 is also a target structure. This portion of the filter housing 102 comprises a multi-metallic catalytic and hydrophilic material, and the hydrophilic surface attracts and absorbs moisture from the surrounding air.

While various embodiments have been described above, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

I claim:

1. An add on filter for a packaged heating, ventilation and/or air conditioning unit including a blower with a blower housing, comprising:
   a filter housing;
   a first mounting unit coupled to the filter housing and including a first magnet to couple the first mounting unit to the blower housing;
   a second mounting unit coupled to the filter housing and including a second magnet to couple the second mounting unit to the blower housing,
   wherein the first mounting unit is approximately V-shaped and the second mounting unit is approximately V-shaped,
   wherein a distance between the first magnet and the second magnet is adjustable; and
   a device for formation of advanced oxidation product disposed in the filter housing, said device for formation of advanced oxidation product including an ultraviolet light source for emitting a broad spectrum of ultraviolet light and a first catalytic target structure mechanically coupled to the ultraviolet light source.

2. The add on filter of claim 1, wherein each of the first mounting unit and the second mounting unit includes at least two magnets.

3. The add on filter of claim 2, wherein each magnet of each mounting unit is independently adjustable relative to the respective mounting unit.

4. The add on filter of claim 2, wherein the first mounting unit is shaped to be mounted on a plurality of blower housings, wherein each of the plurality of blower housings includes a different curvature of radius.

5. The add on filter of claim 1, wherein the first mounting unit includes a first rail and a portion of the first magnet is positioned in the first rail, and the second mounting unit includes a second rail and a portion of the second magnet is positioned in the second rail.

6. The add on filter of claim 5, wherein the first magnet is slidable relative to the first rail and the second magnet is slidable relative to the second rail.

7. The add on filter of claim 6, wherein when the add on filter is mounted to the blower housing the first magnet is fixed relative to the first rail and the second magnet is fixed relative to the second rail.

8. The add on filter of claim 5, wherein the first mounting unit includes a third rail and a portion of a third magnet is positioned in the third rail, and the second mounting unit includes a fourth rail and a portion of a fourth magnet is positioned in the fourth rail.

9. The add on filter of claim 8, wherein the first magnet is slidable relative to the first rail, the second magnet is slidable relative to the second rail, the third magnet is slidable relative to the third rail and the fourth magnet is slidable relative to the fourth rail.

10. The add on filter of claim 9, wherein when the add on filter is mounted to the blower housing the first magnet is fixed relative to the first rail, the second magnet is fixed relative to the second rail, the third magnet is fixed relative to the third rail and the fourth magnet is fixed relative to the fourth rail.

11. The add on filter of claim 1, wherein the filter housing includes a first protrusion and a second protrusion,
wherein the first protrusion forms a first rail with said first mounting unit and a portion of the first magnet is positioned in the first rail, and
wherein the second protrusion forms a second rail with the second mounting unit and a portion of the second magnet is positioned in the second rail.

12. The add on filter of claim 1, wherein the filter housing includes a plurality of openings in a portion of the filter housing surrounding the device for formation of advanced oxidation product.

13. The add on filter of claim 12, wherein the portion of the filter housing including a plurality of openings forms a second catalytic target structure.

14. A system for filtering air in a packaged heating, ventilation and/or air conditioning unit, comprising:
a blower including a blower housing; and
an add on filter coupled to the blower housing to produce an oxidation agent,
wherein the add on filter comprises:
a filter housing;
a first mounting unit coupled to the filter housing and including a first magnet to couple the first mounting unit to the blower housing;
a second mounting unit coupled to the filter housing and including a second magnet to couple the second mounting unit to the blower housing,
wherein the first mounting unit is approximately V-shaped and the second mounting unit is approximately V-shaped,
wherein a distance between the first magnet and the second magnet is adjustable; and
a device for formation of advanced oxidation product disposed in the filter housing, said device for formation of advanced oxidation product including an ultraviolet light source for emitting a broad spectrum of ultraviolet light and a first catalytic target structure mechanically coupled to the ultraviolet light source.

* * * * *